United States Patent
Fulton, III et al.

(10) Patent No.: US 7,479,152 B2
(45) Date of Patent: ***Jan. 20, 2009

(54) TARGET TISSUE LOCALIZATION DEVICE

(75) Inventors: Richard Eustis Fulton, III, Grand Junction, CO (US); William R. Dubrul, Redwood City, CA (US)

(73) Assignee: Artemis Medical, Inc., Hayward, CA (US)

( * ) Notice: Subject to any disclaimer, the term of this patent is extended or adjusted under 35 U.S.C. 154(b) by 571 days.

This patent is subject to a terminal disclaimer.

(21) Appl. No.: 10/885,910

(22) Filed: Jul. 6, 2004

(65) Prior Publication Data

US 2004/0243171 A1 Dec. 2, 2004

Related U.S. Application Data

(63) Continuation of application No. 10/134,802, filed on Apr. 29, 2002, now Pat. No. 6,758,855, which is a continuation of application No. 09/678,508, filed on Oct. 2, 2000, now Pat. No. 6,409,742, which is a continuation of application No. 09/376,678, filed on Aug. 18, 1999, now Pat. No. 6,179,860.

(60) Provisional application No. 60/097,126, filed on Aug. 19, 1998, provisional application No. 60/106,733, filed on Nov. 2, 1998.

(51) Int. Cl.
*A61M 29/00* (2006.01)

(52) U.S. Cl. ........................ 606/200; 606/116

(58) Field of Classification Search ............... 606/200, 606/113, 114, 116, 117, 220, 214, 213, 184, 606/185

See application file for complete search history.

(56) References Cited

U.S. PATENT DOCUMENTS

| 2,816,552 | A | 12/1957 | Hoffman |
| 3,320,957 | A | 5/1967 | Sokolik |
| 3,836,776 | A | 9/1974 | Gullekson |
| 3,996,938 | A | 12/1976 | Clark, III |
| 4,650,466 | A | 3/1987 | Luther |
| 4,799,495 | A | 1/1989 | Hawkins |
| 4,852,568 | A | 8/1989 | Kensey |
| 4,966,583 | A | 10/1990 | Debbas |

(Continued)

FOREIGN PATENT DOCUMENTS

EP 0769281 4/1997

(Continued)

OTHER PUBLICATIONS

EPO Supplementary Search Report, European Patent Application 99943808.8, dated Mar. 6, 2006.

*Primary Examiner*—Kevin T Truong
(74) *Attorney, Agent, or Firm*—Welsh & Flaxman, LLC

(57) ABSTRACT

A target tissue localization device includes a tubular mesh anchor element that is secured to a placement device. In use, the localization device is passed through the patient's skin to the target tissue, creating a tissue track. The tubular mesh anchor element is located at the target tissue and expanded from a contracted to an expanded configuration. Methods for localizing a lymph node are also described. After determining the position of the lymph node, a localization device, which includes an anchor element, is localized near or within the lymph node. The anchor element is then expanded.

6 Claims, 6 Drawing Sheets

U.S. PATENT DOCUMENTS

| | | |
|---|---|---|
| 4,986,279 A | 1/1991 | O'Neill |
| 5,031,634 A | 7/1991 | Simon |
| 5,059,197 A | 10/1991 | Urie |
| 5,158,565 A | 10/1992 | Marcadis |
| 5,183,463 A | 2/1993 | Debbas |
| 5,195,533 A | 3/1993 | Chin |
| 5,221,269 A | 6/1993 | Miller |
| 5,336,191 A | 8/1994 | Davis |
| 5,365,943 A | 11/1994 | Jansen |
| 5,382,259 A | 1/1995 | Phelps |
| 5,383,892 A | 1/1995 | Cardon |
| 5,396,897 A | 3/1995 | Jain |
| 5,466,225 A | 11/1995 | Davis |
| 5,487,392 A | 1/1996 | Haaga |
| 5,507,769 A | 4/1996 | Marin |
| 5,527,276 A | 6/1996 | Bruce |
| 5,562,725 A | 10/1996 | Schmitt |
| 5,571,091 A | 11/1996 | Davis |
| 5,595,185 A | 1/1997 | Ehrlich |
| 5,603,722 A | 2/1997 | Phan |
| 5,665,092 A | 9/1997 | Mangiardi |
| 5,720,764 A | 2/1998 | Naderlinger |
| 5,728,133 A | 3/1998 | Kontos |
| 5,769,816 A | 6/1998 | Barbut |
| 5,795,308 A | 8/1998 | Russin |
| 5,800,409 A | 9/1998 | Bruce |
| 5,800,445 A | 9/1998 | Ratcliff |
| 5,807,276 A | 9/1998 | Russin |
| 5,810,744 A | 9/1998 | Chu |
| 5,810,849 A | 9/1998 | Kontos |
| 5,810,874 A | 9/1998 | Lefebvre |
| 5,814,064 A | 9/1998 | Daniel |
| 5,827,312 A | 10/1998 | Brown |
| 5,827,324 A | 10/1998 | Cassell |
| 5,855,585 A | 1/1999 | Kontos |
| 5,876,411 A | 3/1999 | Kontos |
| 5,879,357 A * | 3/1999 | Heaton et al. ............. 606/116 |
| 5,916,145 A | 6/1999 | Chu |
| 5,928,260 A | 7/1999 | Chin |
| 5,928,261 A | 7/1999 | Ruiz |
| 6,053,876 A | 4/2000 | Fisher |
| 6,136,014 A | 10/2000 | Sirimanne |
| 6,152,144 A * | 11/2000 | Lesh et al. ............. 606/200 |
| 6,161,034 A | 12/2000 | Burbank |
| 6,238,412 B1 | 5/2001 | Dubrul |
| 6,261,241 B1 | 7/2001 | Burbank |
| 6,277,083 B1 | 8/2001 | Eggers |
| 6,312,429 B1 | 11/2001 | Burbank |
| 6,325,812 B1 * | 12/2001 | Dubrul et al. ............. 606/185 |
| 6,331,166 B1 | 12/2001 | Burbank |
| 2002/0007130 A1 | 1/2002 | Burbank |

FOREIGN PATENT DOCUMENTS

| | | |
|---|---|---|
| EP | 0966920 | 12/1999 |
| GB | 2020557 | 11/1979 |
| WO | WO 97/20504 | 6/1997 |
| WO | WO 98/08441 | 3/1998 |
| WO | WO 99/04704 | 2/1999 |
| WO | WO 99/44506 | 9/1999 |
| WO | WO 00/12009 | 3/2000 |
| WO | WO 00/12010 | 3/2000 |

* cited by examiner

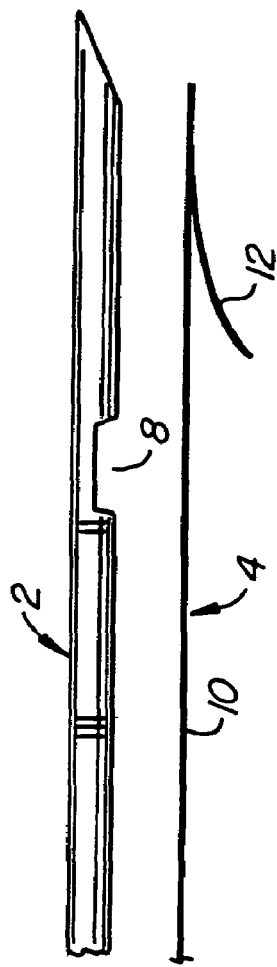
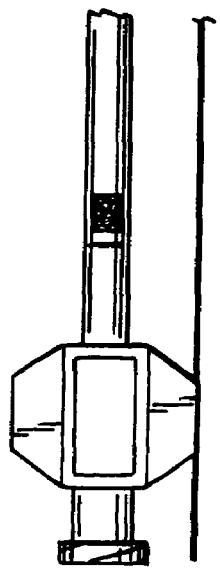
FIG. 1. *PRIOR ART*
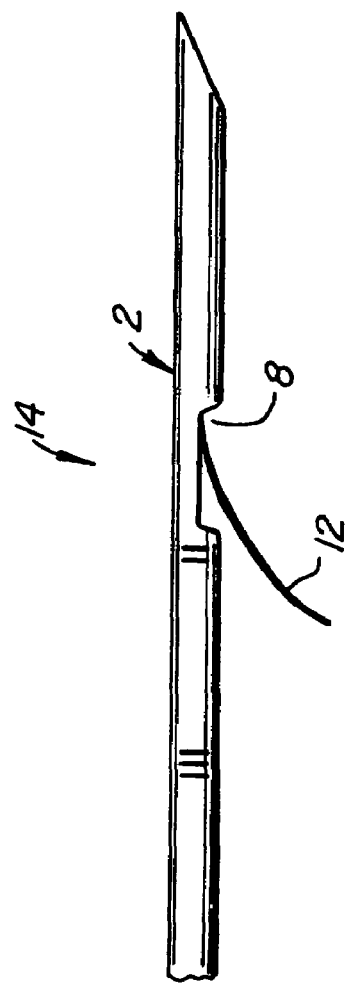
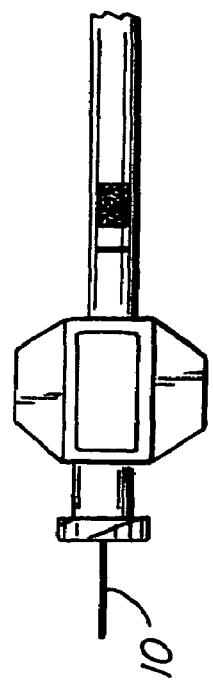
FIG. 2. *PRIOR ART*

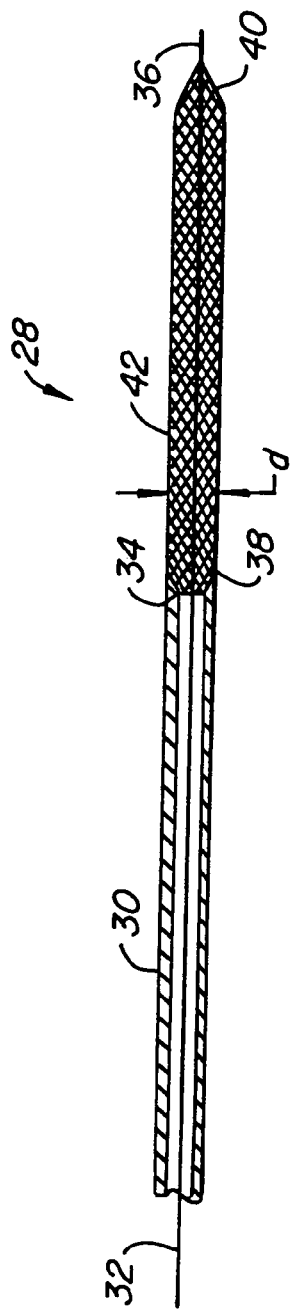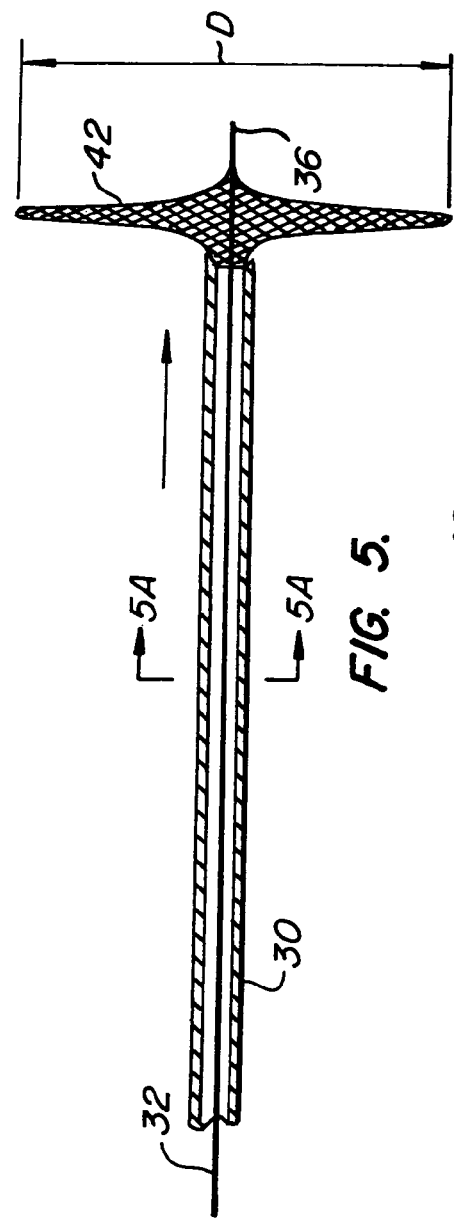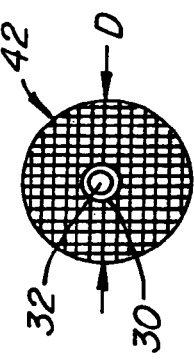

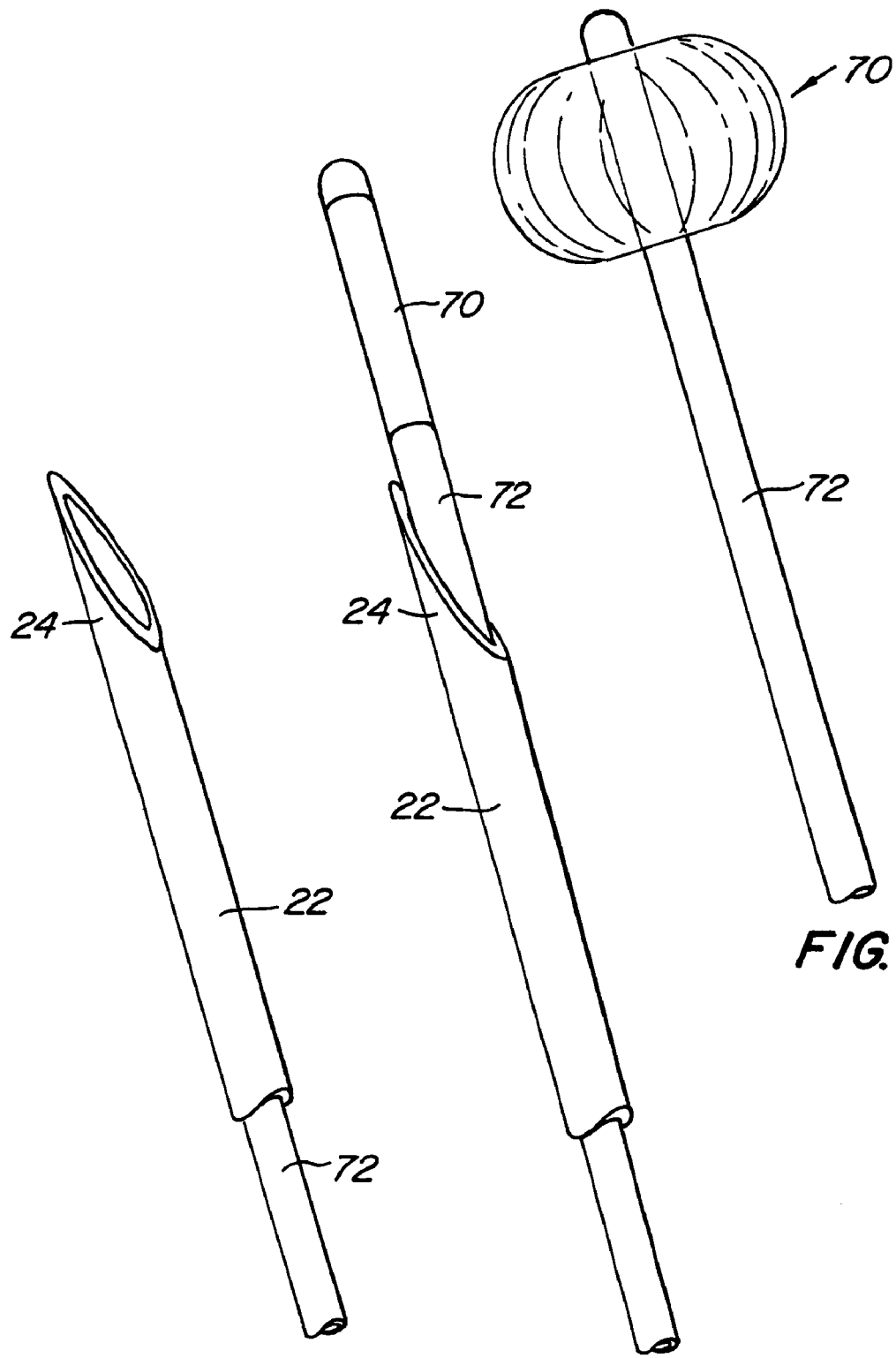

TARGET TISSUE LOCALIZATION DEVICE

This application is a continuation of U.S. application Ser. No. 10/134,802, filed on Apr. 29, 2002 now U.S. Pat. No. 6,758,855, which is a continuation of U.S. application Ser. No. 09/678,508, filed on Oct. 2, 2000, now U.S. Pat. No. 6,409,742, which is a continuation of U.S. patent application Ser. No. 09/376,678, filed on Aug. 18, 1999, now U.S. Pat. No. 6,179,860, which patent claims the benefit of the following Provisional Patent Applications: Biopsy Localization Device, Application No. 60/097,126, filed Aug. 19, 1998 and Biopsy and Tissue Localization Device, Application No. 60/106,733, filed Nov. 2, 1998, by FULTON, Richard E. All of the above-mentioned patents and applications are herein expressly incorporated by reference in their entirety.

BACKGROUND

In the U.S. alone approximately one million women will have breast biopsies because of irregular mammograms and palpable abnormalities. Biopsies can be done in a number of different ways for non-palpable lesions, including surgical excisional biopsies and stereotactic and ultrasound guided needle breast biopsies. In the case of image directed biopsy, the radiologist or other physician takes a small sample of the irregular tissue for laboratory analysis. If the biopsy proves to be malignant, additional surgery (typically a lumpectomy or a mastectomy) is required. In the case of needle biopsies, the patient then returns to the radiologist a day or two later where the biopsy site (the site of the lesion) is relocated by method called needle localization, a preoperative localization in preparation for the surgery.

Locating the previously biopsied area after surgical excision type of biopsy is usually not a problem because of the deformity caused by the surgery. However, if the biopsy had been done with an image directed needle technique, as is common, help in relocating the biopsy site is needed. One procedure to permit the biopsy site to be relocated by the radiologist during preoperative localization is to leave some of the suspicious calcifications; this has its drawbacks.

Another way to help the radiologist relocate the biopsy site involves the use of a small metallic surgical clip, such as those made by Biopsys. The metallic clip can be deployed through the biopsy needle, and is left at the biopsy site at the time of the original biopsy. With the metallic clip as a guide, the radiologist typically inserts a barbed or hooked wire, such as the Hawkins, Kopans, Homer, Sadowski, and other needles, back into the patient's breast and positions the tip of the wire at the biopsy site using mammography to document the placement. The patient is then taken to the operating room with the needle apparatus sticking out of the patient's breast. While the clip provides a good indication of the biopsy site to the radiologist during preoperative localization, the clip remains permanently within the 80% of patients with benign diagnoses. Also, because the clip is necessarily attached to a single position at the periphery of the biopsy site, rather than the center of the biopsy site, its location may provide a misleading indication of the location of diseased tissue during any subsequent medical intervention. The clip is also relatively expensive. In addition, the soft nature of breast tissue permits the tip of the barbed or hooked needle to be relatively easily dislodged from the biopsy site. The surgeon typically pulls on the needle to help locate the area to be removed. This pulling motion during the excision may be responsible more than any other single factor for the movement of the needle. Additionally, these devices are not easily felt by external palpation and the tip is difficult to locate without dissection into the tissues; this prevents a surgical approach which may be more cosmetically advantageous and surgically appropriate than dissecting along the tract of the needle.

Another localization method involves the use of laser light from the tip of a optical fiber connected to a laser. A pair of hooks at the tip of the optical fiber secures the tip at the biopsy site; the glow indicates the position of the tip through several centimeters of breast tissue. This procedure suffers from some of the same problems associated with the use of barbed or hooked wires. Another preoperative localization procedure injects medical-grade powdered carbon suspension from the lesion to the skin surface. This procedure also has certain problems, including the creation of discontinuities along the carbon trail.

SUMMARY OF THE INVENTION

The present invention is directed to a target tissue localization device including an elongate placement device having first and second members being longitudinally movable relative to one another. An anchor is secured to the first and second members and is movable from a first, radially contracted configuration to a second, radially expanded configuration. The placement device and anchor are sized and configured for use in localization of target tissue. According to one aspect of the invention the anchor is a tubular mesh anchor. According to another aspect of the invention the anchor has a sufficiently large cross-sectional area when in the second, radially expanded configuration to substantially eliminate inadvertent dislodgment of the anchor once radially-expanded.

A further aspect of the invention relates to a method for localizing target tissue including determining the location of the target tissue and passing the distal end of an elongate localization device through the patient's skin and to the target tissue to create a tissue track between the patient's skin and the target tissue. The target tissue includes a near side toward the patient's skin and a far side opposite the near side. The localization device includes an anchor element secured to a placement device, the placement device extending from the anchor element along the tissue track and through the patient's skin. The anchor element is located at the target tissue and expanded to an expanded configuration. According to one aspect of the method the anchor element is located on the far side of the target tissue. According to another aspect of the method, the localization device is selected with an anchor which is palpable at the patient's target tissue so that the target tissue can be relocated at least in part by palpation of the patient to locate the anchor; according to this aspect of the invention, at least a sample of the relocated target tissue is removed. The elongate localization device can be used as a guide or guide wire for further diagnostic of therapeutic procedures.

In preferred embodiment of the invention the anchor is a tubular mesh anchor which can be placed into a disk-like shape when in the fully expanded configuration or in a more flattened spherical shape, that is not as flat as the disk-like shape, which may aid in palpability. The anchor may also be in other forms such as a Malecot-type of radially expandable anchor. Another anchor embodiment could be deployed from the end of a hollow sheath and include numerous resilient curved projections which extend generally radially outwardly to fully surround the sheath.

The invention may find particular utility as an aid in the removal of small, difficult-to-grasp body structures, such as lymph nodes or other tissue that is difficult to grasp. The anchor could be positioned behind or inside a lymph node targeted for removal; lymph node removal can be aided by leaving the anchor in its expanded position so that after the surgeon cuts down to the lymph node, the lymph node, some surrounding tissue and the entire localization device can be removed for further analysis.

In some situations the anchor may be left in a partially or fully radially-expanded condition and used to pull the target tissue from the patient, typically with the aid of the surgeon opening the tissue track. For example, for tumor removal of the breast, the anchor may be used in a partially or fully expanded condition so that the tumor and surrounding margins can be removed during lumpectomy. Similar procedures can be used in regions other than the breast.

The invention may also include structure which may enhance ultrasound visibility. Invention may include certain treatment, grooves, slits, or other structure to enhance the ultrasonic visibility of the placement device or the delivery needle, or both. Also, the mesh anchor may provide sufficient reflectivity so that treatment of the placement device and delivery needle is not required. Other techniques for enhancing remote visualization, such as radiopaque markers, can also be used.

The invention is primarily related to mammographic localization, but may find utility with other areas of imaging including ultrasound, thoracoscopy, nuclear medicine, MRI, computed tomography, plain film and any other image guided technology.

The present invention provides a simple, relatively inexpensive, very stable localization device to locate a lesion or other target tissue, typically within the breast of a patient, for subsequent biopsy, excision, intervention, or other purpose. The localization device is easy to insert, deploy, reposition if needed, and remains anchored at the target site substantially better than conventional localization needles. Further, the invention aids relocation of the target tissue by being configured to permit location by palpation by the surgeon in the operating suite. This permits the surgeon to proceed using much less radical techniques, which may be both cosmetically and surgically advantageous.

Other features and advantages of the invention will appear from the following description in which the preferred the embodiments have been set forth in detail in conjunction with the accompanying drawings.

BRIEF DESCRIPTION OF THE DRAWINGS

FIG. 1 illustrates a conventional hollow insertion needle and hook wire;

FIG. 2 illustrates the hook wire of FIG. 1 inserted into the insertion needle with the barb extending through the opening in the insertion needle;

FIG. 4 is a partial cross-sectional view of the distal portion of the localization device of FIG. 2 with the anchor in a radially contracted configuration;

FIG. 5 illustrates the localization device of FIG. 4 with the anchor moved to a radially expanded configuration by the movement of the distal ends of the outer sleeve member and the inner wire member towards one another;

FIG. 5A is a cross-sectional view taken along line 5A-5A of FIG. 5;

FIG. 11 illustrates a further alternative embodiment of the invention in which the anchor is in the form of an expandable balloon, the balloon mounted to the distal end of a shaft, the balloon-type anchor and distal shaft end housed within a delivery needle;

FIG. 11A illustrates the embodiment of FIG. 11 which the balloon-type anchor is in its radially-contracted condition and is positioned past the sharpened tips of the delivery needle; and FIG. 11B illustrates the shaft and balloon-type anchor of FIG. 11A with the balloon-type anchor in its radially-expanded, deployed condition.

DESCRIPTION OF THE SPECIFIC EMBODIMENTS

Figure 3:
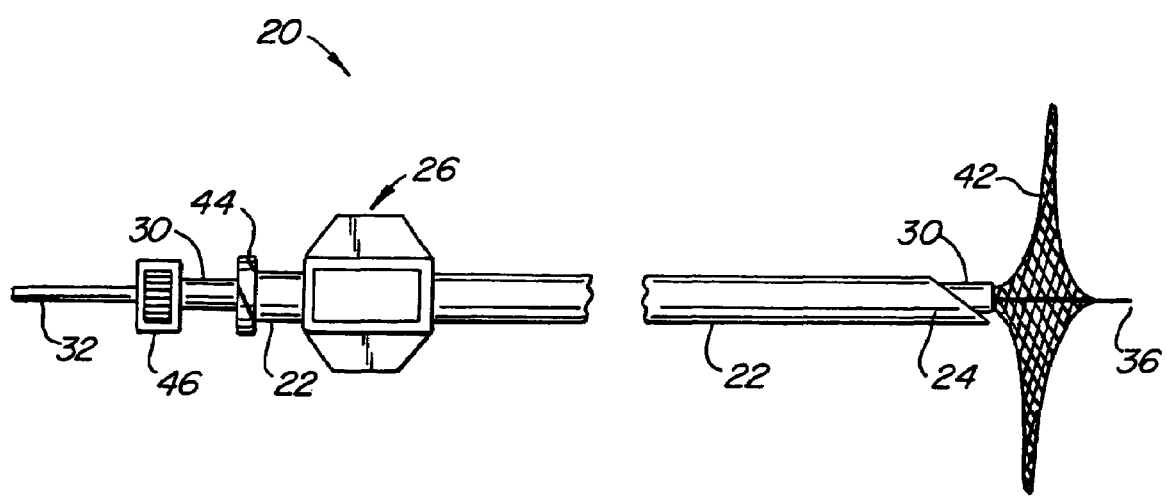
FIG. 3 is an overall view of a localization assembly made according to the invention with the anchor in a radially expanded, deployed condition.

FIG. 1 illustrates a conventional hollow insertion needle 2 placed next to its associated hook wire 4. Insertion needle 2 has a sharpened tip 6 and an opening 8 set back away from tip 6. Hook wire 4 includes a shaft 10 and a barb 12 extending off the distal end of the shaft. Insertion needle 2 is relatively stiff or rigid while hook wire 4 is flexible but resilient. FIG. 2 illustrate the localization assembly 14 made up of the insertion needle 2 and hook wire 4 of FIG. 1 with the barb 12 extending from opening 8. The condition of localization assembly 14 in FIG. 2 is that which would be after tip 6 of insertion needle 2 has been properly placed relative to the target tissue and hook wire 4 has been pulled proximally causing barb 12 to extend from opening 8 and pass into the patient's tissue. As discussed above, this reliance on a thin barb 12 to ensure that assembly 14 does not move after placement is not particularly well-founded; breast tissue is generally quite soft and permits barb 12 to be easily dislodged from its initial position thus providing the surgeon a false indication of the target tissue location.

FIG. 3 illustrates a localization assembly 20 made according to the invention. Assembly 20 includes broadly a hollow delivery needle 22 having a sharpened tip 24 at its distal end and a hub 26 at its proximal end. Needle 22 houses a localization device 28, see FIGS. 4, 5 and 5A, the localization device including an outer sleeve member 30 and an inner wire member 32. The distal ends 34, 36 of outer sleeve member 30 and inner wire member 32 are secured to the proximal and distal ends 38, 40 of a tubular mesh anchor 42, respectively. The relative positions of hollow delivery needle 22 and outer sleeve member 30 can be locked in place by a needle/sleeve locking device 44 while the relative positions between outer sleeve member 30 and inner wire member 32 can be secured by a sleeve/wire locking device 46. Anchor 42 is moved from its radially contracted condition of FIG. 4 to its radially expanded condition of FIGS. 3 and 5 by pulling on inner wire member 32 while maintaining outer sleeve member 30 in place, or by pushing on outer sleeve member 30 while maintaining inner wire member 32 in place, or by both pulling on inner wire 32 and pushing on outer sleeve 30 as suggested by the arrows in FIG. 5.

Localization assembly 20 is preferably made from conventional biocompatible materials, such as stainless steel for delivery needle 22, outer sleeve member 30 and inner wire member 32. Anchor 42 is preferably made of stainless steel or NiTi or a polymer such as Kynar, polyester, nylon, etc., and may be coated with a material such as PTFE or other lubricious coating, such as hydrophilic or hydrophobic coating commonly used in medical devices, to help anchor 42 pass through the patient's tissue both when in the radially contracted condition of FIG. 4 and when moved to the radially expanded condition of FIG. 5. The mesh material of mesh anchor 42 preferably has a tight enough weave so that it provides substantial hindrance to passage of the patient's tissue, typically at a breast tissue, through the anchor when in the radially expanded condition of FIGS. 3 and 5. Tubular mesh anchor 42 may be somewhat porous or it could be substantially impervious to fluid flow. Anchor 42 could be, for example, covered with a flexible elastic film to provide fluid impermeability in the expanded condition.

In one embodiment anchor 42 is made of wires, or filaments or yarns having a diameter of 0.13 mm (0.005 inch) and spacing of 0.025 mm (0.001 inch) in its contracted condition of FIG. 4. Mesh anchor 42 is preferably made from wires or other elements have diameters of about 0.025 to 0.38 mm (0.001 to 0.015 inch) and a contracted condition spacing of about 0.0025 to 0.051 mm (0.0001 to 0.002 inch). The length of anchor 42 is a large factor in determining how large anchor 42 is when in the radially expanded condition of FIGS. 5 and 5A. That is, a tubular anchor 42 having a relatively short length when in the radially contracted condition of FIG. 4 will have a smaller diameter D when in the radially expanded condition of FIGS. 5 and 5A as opposed to an anchor with a longer axial length when in the radially contracted condition of FIG. 4.

The cross-sectional area D diameter of anchor 42 in the radially expanded condition of FIGS. 5 and 5A, equal to $\pi D^2 \div 4$, is preferably at least four times and more preferably at least eight times the cross-sectional area of anchor 42 in the radially contracted condition of FIG. 4, equal to $\pi D^2 \div 4$. Another way of defining the enhanced stabilization created by anchor 42 is based upon the force it would take to substantially dislodge the anchor from a deployed position within the patient's breast. Conventional hooked wire embodiments such as that of FIGS. 1 and 2, which commonly become substantially dislodged when a longitudinally directed pulling force of only about 0.5 to 2 kg (1 to 4 pounds) is exerted on localization assembly 14. Anchor 42, due to its large surface area opposing any axially-directed force, requires a longitudinally directed pulling force on outer sleeve 30 and inner wire member 32 to be substantially more than the force required to substantially dislodge a hooked wire localization needle to be substantially dislodged from breast tissue.

Figure 6:
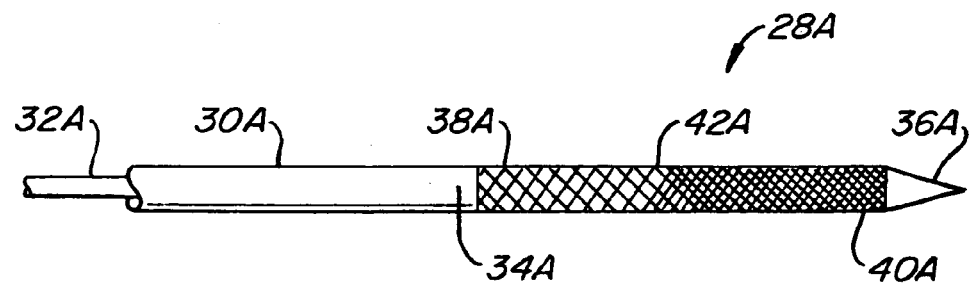
FIG. 6 illustrates a further embodiment of the localization device of FIG. 4 in which the inner wire member has been replaced by an inner shaft member having a pointed distal end to potentially eliminate the need for the delivery needle of FIG. 3.
Figure 7:
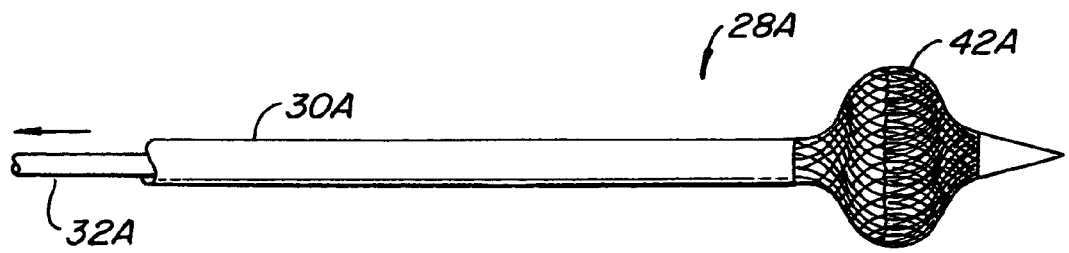
FIG. 7 illustrates the device of FIG. 6 with the anchor in a first radially expanded condition, the anchor forming a somewhat flattened spherical shape.
Figure 8:
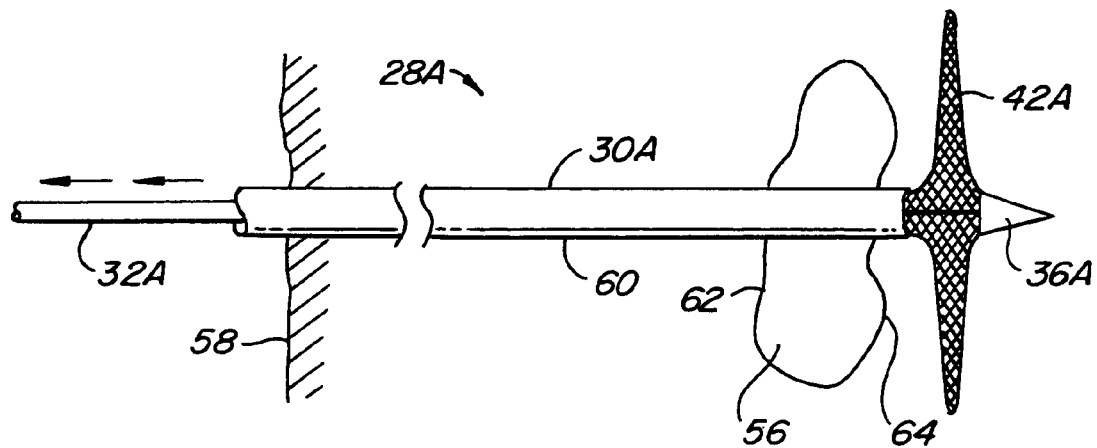
FIG. 8 illustrates the localization device of FIG. 7 with the anchor in a fully radially expanded configuration in the shape of a generally flat disk, the anchor illustrated positioned on the far side of a lesion or other target tissue.

An alternative embodiment of the localization assembly is shown in FIG. 6 with like reference numerals referring to like elements. Localization device 28A is designed to potentially eliminate the need for the hollow delivery needle 22 of FIG. 3. Outer sleeve 30A is essentially the same with an inner shaft 32A replacing inner wire 32. The distal end 36A of inner shaft 32A is a sharpened point to aid piercing the patient's tissue. The tubular mesh anchor 42A is secured at its distal and proximal ends 40A and 38A to distal end 36A of inner shaft 32A and distal end 34A of outer sleeve 30A. FIG. 7 illustrates result of collapsing anchor 42A about half way resulting in a generally flatten spherical shape or ellipsoid of revolution shape. This shape does not create as large a cross-sectional area but may be useful in aiding palpability of anchor 42A. FIG. 8 illustrates the result of continuing to collapse inner mesh anchor 42A by pulling on inner shaft member 32A; doing so results in anchor 42A being similar in shape to anchor 42 of FIGS. 5 and 5A.

Figures 9, 10:
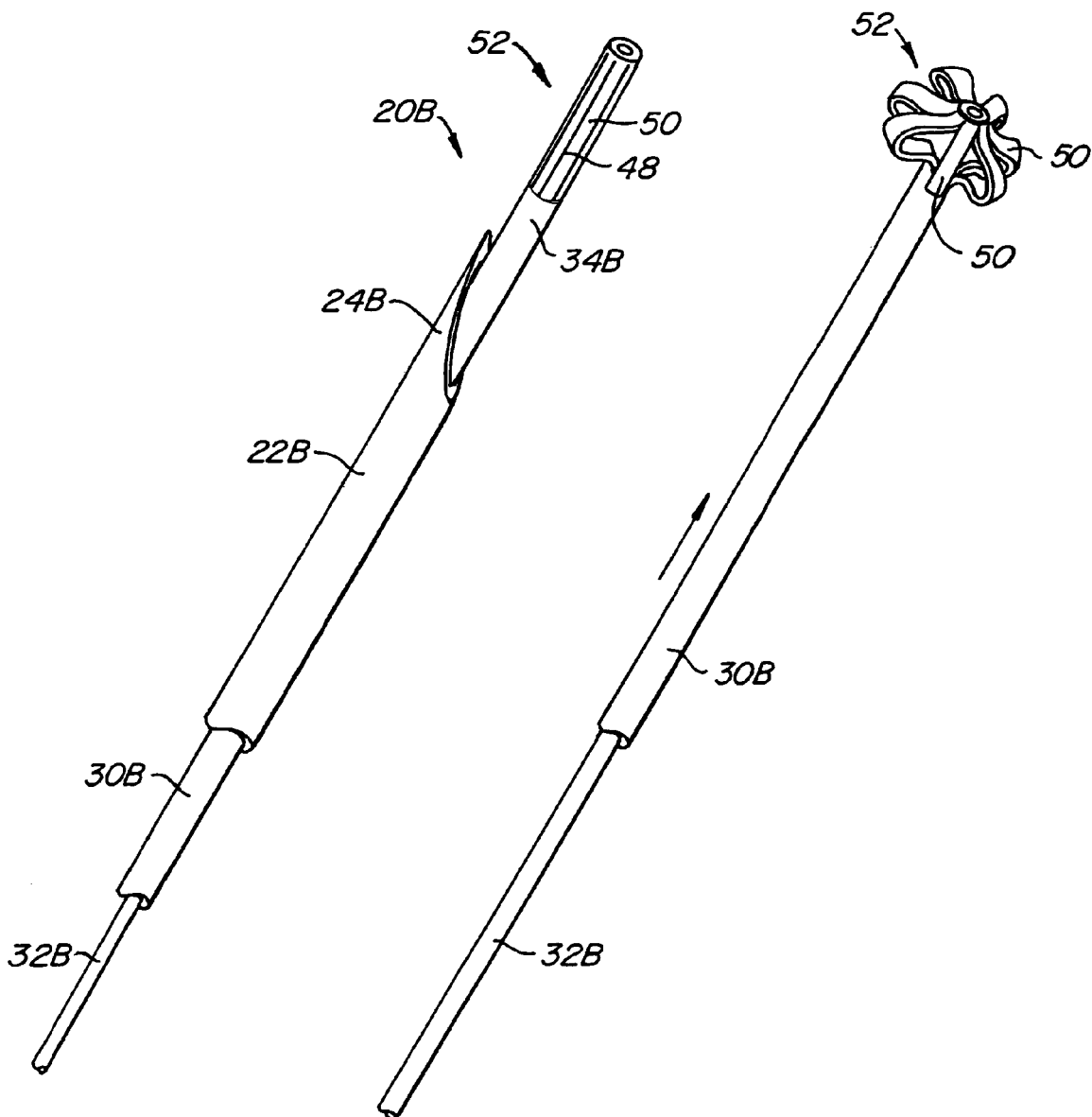
FIG. 9 illustrates an alternative embodiment of the localization assembly of FIG. 3 in which the localization device of FIG. 3 has been replaced by a localization device having an inner shaft member and an outer shaft member, the outer shaft member having a series of longitudinally extending slits formed at its distal end.
FIG. 10 illustrates the localization device of FIG. 9 with the inner shaft member pulled relative to the outer sleeve member causing the sleeve segments to expand radially to form a Malecot-type anchor.

A further embodiment of the invention is illustrated in FIGS. 9 and 10. In FIG. 9, a localization assembly 20B is seen to include a delivery needle 22B housing a localization device 28B. Localization device 28B includes an outer sleeve member 30B and an inner shaft member 32B. The distal end 34B of outer shaft member 30B has a member of axially-extending slits 48 formed therein to define a plurality, preferably six to ten, sleeve segments 50 therebetween. Pulling inner shaft member 32B relative to outer shaft member 30B causes sleeve segments 50 to buckle outwardly to create a Malecot-type anchor 52. To improve the effective cross-sectional area of anchor 52 in the radially-expanded condition, sleeve segments 50 could be surrounded by an expandable mesh or a film which would effectively cover or fill the regions between sleeve segments 50 when in the expanded condition of FIGS. 10 and 10A.

The invention may be used in a manner similar to conventional localization devices. The location of the target tissue 56, see FIG. 8, is determined using, for example, mammography, ultrasound, or other conventional or unconventional techniques. Using the embodiment of FIGS. 6-8 as an example, localization device 28A is passed through skin 58 to create a tissue path 60 between target tissue 56 and the skin. Target tissue 56 has a near side 62 towards skin 58 and a far side 64 away from near side 62, that is facing anchor 42A in FIG. 8. Once in the expanded condition of FIG. 8, localization device 28A is very resistant to being moved or dislodged so that anchor element 42A remains where positioned, in this example on the far side of target tissue 56. Locking device 46 is used to maintain the relative axial positions of outer sleeve member 30 and inner shaft member 32A. In example FIG. 8, localization device 28A is shown having pierced through target tissue 56. In appropriate cases localization device 28A could be positioned to one side of target tissue 56 with anchor 42A opposite far side 64. Distal end 36A could also be positioned opposite near side 62 so that the localization device 28A does not pierce target tissue 56 and anchor 42A lies opposite near side 62 rather than far side 64. The surgeon can relocate target tissue 56 using localization 28A in several ways. First, when anchor 42A is constructed for palpability, the surgeon may determine the location of target tissue 56 by palpation by sensing the presence and location of anchor 42A, anchor 42A being harder than the surrounding tissue. Remote visualization techniques could also be used to determine the location of anchor 42A and thus of target tissue 56. Appropriate therapeutic or diagnostic procedures, such as taking biopsy samples of target tissue 56 or completely removing target tissue 56, can then be accomplished. In some situations localization device 28A will remain in position until anchor 42A is transformed from its radially-expanded condition of FIG. 8 to its radially-contracted condition of FIG. 6, at which time device 28A can be removed from the patient. At other times anchor 42A will remain in its fully radially deployed condition as localization device 28A is used to help pull target tissue 56 along tissue path 60, which may or may not occur after surgical intervention.

A further embodiment of the invention is shown in FIGS. 11-11B. This embodiment uses a balloon-type anchor 70 at the distal end of a hollow delivery shaft 72. Anchor 70 is delivered to a target site while housed within a hollow delivery needle 22 as shown in FIG. 11. Once at the proper location, anchor 70 is exposed, as shown in FIG. 11A, by pushing on shaft 72, pulling on needle 22, or both. FIG. 11B shows balloon-type anchor 70 in its radially-expanded, deployed condition, a flattened spherical shape in this embodiment. Balloon anchor 70 may be made of elastic or inelastic material and can be made to assume a variety of shapes when in the expanded condition. Such shapes include the disk-like shapes FIGS. 3, 5, 5A, the flattened spherical shaped FIGS. 7 and 11B, star-shaped with radially extending fingers (not shown) or other shapes suitable for the surrounding tissue in which it is deployed and the circumstances of its use.

Modification and variation can be made to the disclosed embodiments without departing from the subject of the invention as defined in the following claims.

Any and all patents, patent applications and printed publications referred to above are incorporated by reference.

What is claimed is:

1. A method for localizing a target tissue, comprising the steps of:

determining the location of the target tissue;

passing a distal end of an elongate localization device through the patient's skin and to the target tissue to create a tissue track between the patient's skin and the target tissue, the localization device comprising a tubular mesh anchor element secured to a placement device, the placement device extending from the tubular mesh anchor element, along the tissue track and through the patient's skin;

locating the tubular mesh anchor element at the target tissue;

expanding the tubular mesh anchor element from a contracted to an expanded configuration; and wherein the cross-sectional area of the tubular mesh anchor element in the expanded configuration is at least four times the cross-sectional area in the contracted state.

2. The method of claim 1, further comprising the steps of:

relocating the target tissue using the localization device; and removing at least a sample of the relocated target tissue.

3. The method of claim 2, wherein the relocating step is carried out using imaging technology.

4. The method of claim 3, wherein the imaging technology is selected from the group consisting of ultrasound, thoracoscopy, nuclear medicine, MRI, computed tomography, and plain film.

5. The method of claim 1, wherein the tubular mesh anchor is positioned on the far side of the target tissue.

6. The method of claim 1, wherein the tubular mesh anchor is positioned on the near side of the target tissue.

* * * * *